United States Patent [19]

Anis

[11] 4,251,887
[45] Feb. 24, 1981

[54] POSTERIOR CHAMBER CAPSULAR LENS IMPLANT AND METHOD FOR IMPLANTATION OF THE LENS

[76] Inventor: Aziz Y. Anis, 7531 N. Hampton, Lincoln, Nebr. 68506

[21] Appl. No.: 25,708

[22] Filed: Apr. 2, 1979

[51] Int. Cl.³ .............................. A61F 1/16; A61F 1/24
[52] U.S. Cl. ......................................... 3/13; 128/303 R
[58] Field of Search ............................................. 3/13, 1

[56] References Cited

U.S. PATENT DOCUMENTS

| | | |
|---|---|---|
| 3,673,616 | 7/1972 | Fedorov et al. ............................ 3/13 |
| 3,906,551 | 9/1975 | Otter ........................................ 3/13 |
| 3,913,148 | 10/1975 | Potthast .................................... 3/13 |
| 3,922,728 | 12/1975 | Krasnov .................................... 3/13 |
| 3,925,825 | 12/1975 | Richards et al. ......................... 3/13 |
| 3,971,073 | 7/1976 | Richards et al. ......................... 3/13 |
| 3,986,214 | 10/1976 | Krasnov .................................... 3/13 |
| 3,994,027 | 11/1976 | Jensen et al. ............................. 3/13 |
| 4,010,496 | 3/1977 | Neefe ........................................ 3/13 |
| 4,012,823 | 3/1977 | Richards ................................... 3/13 |
| 4,073,015 | 2/1978 | Peyman et al. ........................... 3/13 |
| 4,110,848 | 9/1978 | Jensen ...................................... 3/13 |
| 4,159,546 | 7/1979 | Shearing ................................... 3/13 |

FOREIGN PATENT DOCUMENTS 2717706 10/1978 Fed. Rep. of Germany ................ 3/13

OTHER PUBLICATIONS

"Covered Bridge an Update on Lens Implantation", by John H. Sheets or Bridge Over Troubled Waters (Book), 1977, pp. 5-13, (Little-Arnott-Posterior Lens on p. 12 Relied Upon).
The Lens (Publication Sheet) Model 42p and Model 101 Relied Upon, Published 1977.

*Primary Examiner*—Ronald L. Frinks
*Attorney, Agent, or Firm*—Henderson & Sturm

[57] ABSTRACT

A posterior chamber capsular lens implant and apparatus for implantation of the lens are utilized in a surgical method following a capsulectomy to remove a cataract impaired natural lens. The lens implant has a plane surface and a convex surface. The entire lens is fitted within the capsule of the posterior chamber. Affixed opposite each other within and along the peripheral edge of the lens are a pair of plastic, kidney shaped loops. The method for implanting the lens provides the steps of forming a triangular capsulectomy, extracting the cortical lens matter and any posterior subcapsular plaque matter from the capsular bag, and then inserting the lens implant. The insertion is accomplished by utilizing a plastic sleeve apparatus in conjunction with an irrigating canula. The loops of the lens implant maintain a centralized location of the lens within the posterior chamber capsule thereby eliminating any need for fixating sutures within the eye itself.

4 Claims, 5 Drawing Figures

U.S. Patent        Feb. 24, 1981        4,251,887

POSTERIOR CHAMBER CAPSULAR LENS IMPLANT AND METHOD FOR IMPLANTATION OF THE LENS

BACKGROUND OF THE INVENTION

This invention is a posterior chamber capsular lens implant and a method and apparatus for the implantation of the lens within the posterior chamber of the eye.

Surgical extraction of a cataract impaired lens of the human eye is a medical procedure under much research at the present time. Complete visual performance of the eye is the objective sought from such a procedure. To achieve this objective, the natural lens can be removed and an artificial lens then implanted within the eye. Due to the structure of the eye, the implant must be located either in the eye's anterior chamber or in its posterior chamber. Posterior chamber lens implants provide the most natural and effective substitute for the removed original lens of the eye.

Prior art for posterior chamber lenses reveal major disadvantages. One of such disadvantages is the requirement that sutures be fixed inside the eye in order to centralize the location of the lens implant. Another is placement of the lens implant in front of the capsular bag resulting in impact against the vascular tissues of the ciliary body.

Examples of the prior art posterior lenses are few. The Pearce posterior chamber lens is a lens with three haptics extending from the len's edge. The lens is then sutured into its position within the posterior chamber. The Harris lens is similar to the Pearce lens with primary variance in the number of haptics, having four instead of three.

A lens which does not require the use of fixating permanent sutures, and is a posterior chamber lens implant, is the Shearing lens. A Shearing lens utilizes two opposing incomplete loops attached to the lens at one end and free at the other end to give each loop compressibility and to centralize the lens in front of the capsular bag of the eye. The loops stabilize the centralized location of the lens once it is implanted, but given the structure of the Shearing loops, this stabilization can occur by impacting against the ciliary body. It is possible that the free ends of the len's loops could cause harm to the interior of the eye. Such harm could eliminate the Shearing lens' advantages over posterior chamber lens implants which require the use of sutures to centralize their location.

Thus, the continued requirement of sutures and the location of the implant's impact within the eye necessitated further research for a more effective and safer substitute for the removed natural lens of the human eye.

Accordingly, there exists a need for a sutureless lens implant for the posterior chamber capsule which is self-centering, which can be safely implanted and which remains in position within the capsular bag. The instant invention is directed to that need as it provides a lens, and a method and apparatus for implanting such a lens.

BRIEF SUMMARY OF THE INVENTION

It is a primary object of this invention to provide a posterior chamber capsular lens implant having the means to self-centralize without the use of fixating sutures within the eye.

Another object of the invention is to provide a lens with attached loops.

Another object of this invention is to provide both a method and apparatus for implanting a posterior chamber capsular lens.

It is a further object of this invention to provide a lens to be implanted within the capsular bag which held the original refracting matter of the eye, thereby providing an artificial lens which approaches as closely as possible the natural state of the functioning eye.

Another object of this invention is to eliminate any need for fixating sutures previously required until the capsular adhesions form.

A further object of this invention is to provide a method for implantation of the lens that is not only simple, but requires less surgical maneuvers than those known in the prior art.

A further object is to provide a lens and a method and apparatus for the lens implantation which will cause the minimum amount of irritation to the sensitive portions of the eye.

These and other objects are obtained according to the instant invention by providing an artificial lens implant and a method and apparatus for the implantation of the implant within the posterior chamber capsule of the eye. After performing a triangular capsulectomy, the nucleus and cortical matter are extracted and the lens is implanted by means of a special plastic sleeve apparatus and an irrigating canula. The two kidney shaped plastic loops of the implanted lens maintain, by their flexibility and special shape, the centralized location of the implanted lens within the capsular bag in the posterior chamber of the eye.

BRIEF DESCRIPTION OF THE DRAWINGS

For a better understanding of the invention, as well as other objects and further features thereof, reference is made to the following detailed disclosure of the invention taken in conjunction with the accompanying drawings wherein.

DESCRIPTION OF THE PREFERRED EMBODIMENT

Figure 1:
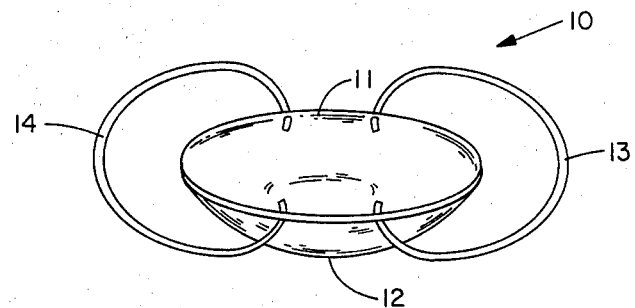
FIG. 1 is a partially perspective side view of the lens implant of the instant invention.
Figure 2:
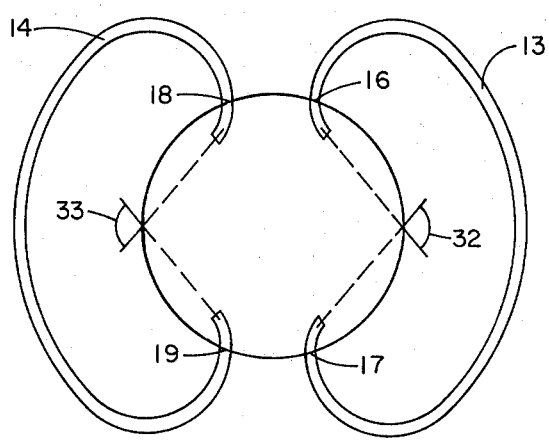
FIG. 2 is a top plan view of the implant of FIG. 1.

Referring now to FIG. 1, the lens implant shown generally by the numeral 10 is featured with an anterior surface plane 11 and a convex posterior surface 12. The lens 10 has two side loops 13 and 14. Each loop is made of a plastic, or other suitable material, possibly a supramid or a polypropylene. The loops are affixed at positions along the lens' edge at specific locations and forming kidney shapes as shown in FIG. 2. The positions at which the loops are fixed at both ends along the lens' edge are at spaced points along the periphery of the lens, each loop extending therebetween and following along the perimeter of the lens body. Thus a kidney shape is formed defining upper and lower knee portions connected by an intermediate portion, said upper and lower knee portions having outermost extensions spaced from each other a distance significantly greater than the distance between the upper and lower peripheral portions of the lens body so as to extend radially above and below said lens periphery. In the embodiment disclosed herein one end of the first loop 13 enters the periphery of the lens tangentially at the 1:30 o'clock position 16 on the lens' edge as it is viewed from the anterior side. The loop 13 then follows along the perimeter of the lens and re-enters the lens' edge at the 4:30 o'clock position 17. Both ends of the loop 13 point toward the 3:00 o'clock position with the linear projections of these ends 32 forming an angle of approximately 100° as shown in FIG. 2. The purpose of the angle projection will be discussed later. An identical loop 14 is formed in substantially the same manner as the first loop 13. The second loop 14 has ends which enter the lens' edge at the 7:30 o'clock position 19. Again, the linear projections of these ends 33 will form a 100° angle, but at the 9:00 o'clock position rather than the 3:00 o'clock position of the first loop 13.

Both of the loops 13 and 14 thus positioned form a kidney shape. With this kidney shape the plastic loops are not only compressible, but also provide a springy action which aids the lens insertion into the capsular bag of the eye and provides a means for maintaining the lens in a centralized position after the insertion is completed. The centralized position is not only important, but vital to the proper functioning of the artificial lens. The special loops of this invention uniquely provide the lens implant with the necessary centralization as each loop impacts against the equator of the capsule between the anterior capsular flap and the posterior capsule. With this impacting, the equalizing spring action of the flexible loops centralizes the implanted lens 10 horizontally. Vertical centralizing is achieved by the long radius curves and upper and lower knees of the loops in much the same manner. Another unique feature of the implant is that further stabilization is achieved in the immediate post-operative period with the loops impacting the capsular equator. This is achieved without the use of fixating sutures and becomes permanent when the natural adhesions form between the anterior and posterior capsular flaps following the implantation. Thus, one of the foremost advantages of this invention is realized with the elimination of the prior art's need for sutures within the eye itself.

The method and apparatus for the implantation of the posterior chamber capsular lens 10 will now be discussed. The pupil of the eye if fully dilated in a manner well known to those skilled in the profession. A first small incision is made at the limbus of the eye structure in order to admit only the cystotome which will outline the triangular capsulectomy. The incision is small so as to maintain the anterior chamber of the eye in order to avoid the collapse of the cornea. Generally, a low intraocular vitreous pressure is achieved by ocular massage. Once the cystotome is inserted into the anterior chamber, the capsulectomy is performed upon the lens capsule in a manner known in the art.

Figure 3:
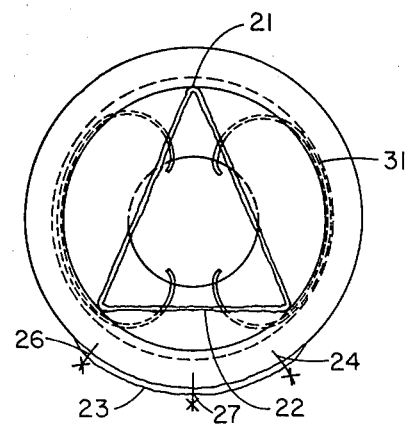
FIG. 3 is a partially schematic front plan view of the eye showing the triangular capsulectomy section and the implanted lens of the instant invention.

FIG. 3 illustrates the triangular capsulectomy as viewed from the surgeon's position. The apex of the triangular section is cut at the 6:00 o'clock location 21 of the original lens when viewed from the front of the eye. The base 22 of the triangular section is then at the 12:00 o'clock position of the original lens as shown in FIG. 3. The first incision is enlarged as shown generally by the numeral 23 in FIG. 3. Two sutures are then placed at the 10:30 o'clock location 24 and the 1:30 o'clock location 26 with a third suture placed at the 12:00 o'clock location 27. The sutures are then looped.

Following the placement of the sutures 24 and 26, the nucleus or hard core of the original lens is expressed out of the anterior chamber. The preplaced sutures are then tied to close the anterior chamber. The remaining cortical lens matter is now aspirated by a technique well known in the art such as the Kelman irrigation tip, the McIntyre co-axial system, or other method. The technique for removal does not matter so long as substantially all of the lens cortical matter is removed and the capsular bag is well cleansed. Posterior subcapsular plaque should also be cleansed from the capsule. Following the aspiration, the middle suture at the 12:00 o'clock position 27 is untied.

Figure 4:
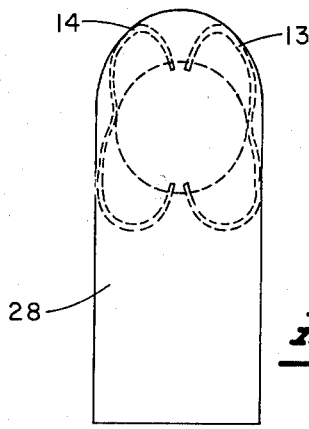
FIG. 4 is a partially schematic view of the plastic sleeve of the instant invention containing the lens implant of the instant invention.

Prior to the time of the surgery, a plastic sleeve 28 in the shape of the Sheet's Glide is made and will serve as an implantation apparatus. Unlike a Sheet's Glide which has only one layer of plastic, and is placed under a lens in order to guide the lens, the plastic sleeve apparatus of this invention is a sleeve with a diameter large enough to hold the lens implant as shown in FIG. 4. The plastic sleeve is rounded at one end and may be formed from plastic steridrape or other suitable material.

Figure 5:
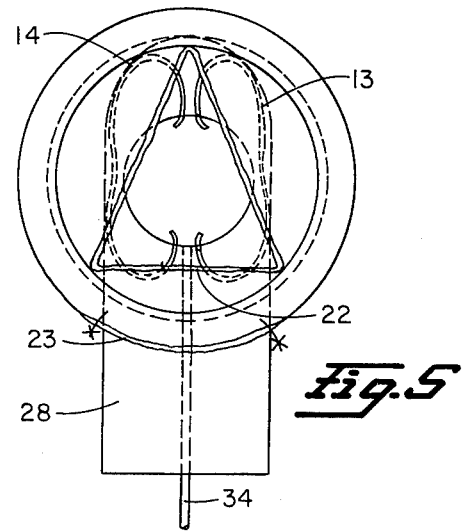
FIG. 5 is a partially schematic view of the eye with the plastic sleeve and the irrigating canula as they insert the lens implant of the instant invention.

Referring now to FIG. 5, immediately after the extra capsular cataract extraction, the sleeve is "loaded" with the lens implant 10. The "loading" consists of the lens implant 10 being passed to the rounded end of the sleeve. The plastic sleeve 28 now containing the lens implant 10 is then introduced, rounded end first, into the eye between the preplaced sutures 26 and 24. The "loaded" sleeve is guided under the anterior capsular flap and then moved into the interior of the now vacant capsular bag. The "loaded" sleeve is inserted until the rounded tip contacts the equator of the capsular bag at the 6:00 o'clock location 21. At this time, an irrigating canula 34 is passed inside the sleeve until it reaches the edge of the lens at the 12:00 o'clock position. The canula then supports the lens implant by one flap on the canula's end opening resting on the anterior side of the lens and the other flap of the canula resting on the posterior side of the lens.

With the canula 34 now supporting the lens 10, the plastic sleeve 28 can be withdrawn from the eye without also withdrawing the lens implant 10. As a plastic sleeve 28 is being withdrawn, the lens remains in the capsular bag with the loops being freed from their compressed positions. As the loops leave the sleeve they resume their normal kidney shape. Once the normal kidney shape is attained, the loops impact against the equator 31 of the capsular bag. This impacting condition stabilizes the position of the lens within the bag, both laterally and longitudinally as discussed earlier. Once the sleeve is fully withdrawn and the loops are once again kidney shaped, the canula 34 may be removed. The implantation is then complete with the closing of the cataract section. Because of the nature of the implanted lens' loops, the capsular bag will then collapse about the loops and adhesions subsequently form further reinforcing the stability and centralized position of the implanted lens within the eye.

The lens implant and the method and apparatus for its implantation as herein described and illustrated includes those changes within the scope and principles of the invention apparent to those skilled in the art upon a reading of this disclosure and is thus not limited by the description of the preferred embodiments but only by the scope of the appended claims.

I claim:

1. A posterior chamber capsular lens implant for implantation within an eye, the lens implant comprising: a plano-convex body having two opposed loops affixed at both ends at spaced points along the periphery of the lens, and extending therebetween following along the perimeter of the lens body in order that each loop will impact against the equator of the capsule between the anterior capsular flap and the posterior capsule, said loops each forming a kidney shape defining upper and lower knee portions connected by an intermediate portion, said upper and lower knee portions having outermost extremities spaced from each other a distance significantly greater than the distance between the upper and lower peripheral portions of the lens body so as to extend radially above and below said lens peripheral portions, whereby the loops each have a long radius curve and upper and lower knees which impact against the equator of the lens capsule in order that the lens implant body will be centralized both horizontally and vertically.

2. The lens implant of claim 1 wherein the said loops are sufficiently compressible both laterally longitudinally for insertion through the base line of a triangular capsulectomy.

3. The lens implant of claim 1 wherein said kidney shape is formed by each end of each loop entering the periphery of the lens more or less tangentially such that the linear projections of these ends will intersect at an intermediate point on the periphery of the lens and form an angle of approximately 100°.

4. A method for implanting a posterior chamber capsular lens comprising the steps of:

providing a plano-convex lens body having a plurality of loops extending from the lens body with the ends of the loops affixed within the lens body;

providing an apparatus which is a sleeve shaped unit having both ends open with one of said ends rounded and of a diameter which will slidably secure the lens implant having compressible loops in a compressed state;

performing a triangular capsulectomy upon the natural refracting lens matter of the eye;

expressing and extracting the cortical lens matter and any posterior subcapsular plaque matter from the lens capsule of the eye;

inserting the sleeve shaped unit containing the lens implant into the posterior chamber of the eye; and implanting the lens implant within the lens capsule of the eye by holding the lens implant with a holding means while withdrawing the sleeve allowing the compressed loops to expand to impact the equator of the lens capsular bag.

* * * * *